(12) United States Patent
Velez Rivera

(10) Patent No.: US 9,186,172 B2
(45) Date of Patent: Nov. 17, 2015

(54) EPIDURAL SPACE LOCATING DEVICE

(76) Inventor: Héctor de Jesús Velez Rivera, Zapopan (MX)

( * ) Notice: Subject to any disclaimer, the term of this patent is extended or adjusted under 35 U.S.C. 154(b) by 1231 days.

(21) Appl. No.: 13/063,838

(22) PCT Filed: Sep. 11, 2009

(86) PCT No.: PCT/IB2009/006833
§ 371 (c)(1),
(2), (4) Date: May 31, 2011

(87) PCT Pub. No.: WO2010/029428
PCT Pub. Date: Mar. 18, 2010

(65) Prior Publication Data
US 2011/0224623 A1 Sep. 15, 2011

(30) Foreign Application Priority Data
Sep. 12, 2008 (MX) .................. MX/a/2008/011713

(51) Int. Cl.
*A61M 5/00* (2006.01)
*A61M 5/31* (2006.01)
*A61B 17/34* (2006.01)
*A61B 17/00* (2006.01)
*A61B 19/00* (2006.01)

(52) U.S. Cl.
CPC ......... *A61B 17/3401* (2013.01); *A61B 17/3403* (2013.01); *A61B 2017/00022* (2013.01); *A61B 2017/00115* (2013.01); *A61B 2019/464* (2013.01)

(58) Field of Classification Search
CPC .......... A61B 5/03; A61B 5/031; A61B 5/032; A61B 5/033; A61B 5/035; A61B 5/036; A61B 5/037; A61B 5/038; A61B 17/3401; A61B 17/3403; A61B 2017/00115; A61B 2017/00022; A61B 2019/464; A61M 5/00
USPC .............. 600/73, 346, 485, 561, 564; 604/66, 604/187, 218, 239
See application file for complete search history.

(56) References Cited

U.S. PATENT DOCUMENTS

| 4,320,767 | A | * | 3/1982 | Villa-Real | 600/493 |
| 5,364,365 | A | * | 11/1994 | Wortrich | 604/158 |
| 5,538,509 | A | * | 7/1996 | Dunlap et al. | 604/264 |
| 5,725,509 | A | * | 3/1998 | Scarfone et al. | 604/217 |
| 2007/0244446 | A1 | * | 10/2007 | Sundar et al. | 604/218 |
| 2009/0326482 | A1 | * | 12/2009 | Hochman | 604/246 |

FOREIGN PATENT DOCUMENTS

| CN | 2852933 Y | 1/2007 |
| KR | 20020028599 A | 4/2002 |
| KR | 20020085263 A | 11/2002 |

(Continued)

*Primary Examiner* — Rene Towa
(74) *Attorney, Agent, or Firm* — Browdy and Neimark, PLLC

(57) ABSTRACT

An epidural space locating device is described, comprising a handle with a proximal end and a distal end; a hollow distal chamber attached to the handle distal end and being provided with a distal connector where a spinal needle is received to be introduced in the patient's body, such that there is a fluid connection between the spinal needle and the distal chamber; the device also comprises a plunger running within the distal chamber from a starting position to a final position when there is a pressure loss within the distal chamber due to the spinal needle has reached the epidural space; the plunger is secured before using the device, which emits a warning signal at the time the epidural space has been reached.

16 Claims, 6 Drawing Sheets

(56) References Cited

FOREIGN PATENT DOCUMENTS

| | | |
|---|---|---|
| WO | WO 9215256 A | 9/1992 |
| WO | WO 2004035104 A2 | 4/2004 |
| WO | WO 2004066853 A2 | 8/2004 |
| WO | WO 2006065818 A1 | 6/2006 |

* cited by examiner

EPIDURAL SPACE LOCATING DEVICE

TECHNICAL FIELD

The present invention is related to the techniques applied in the design of surgical procedures devices and equipment, and more specifically, it is related to an epidural space locating device, which during the epidural anesthesia and analgesia procedures, clearly indicates the surgeon the time when a spinal needle has reached the epidural space of a patient.

BACKGROUND OF THE INVENTION

To create an epidural anesthesia or analgesia, two basic techniques to introduce drugs in the spinal area of a patient may be used, namely; epidural and subdural or subarachnoid. In this kind of surgical procedures, an anesthetic is injected in the spinal cord and in the nerve roots to block the pain feelings in a body region, such as the abdomen, hips, legs, or pelvis during labor.

As said medical techniques implies some risks for the patients, it is important to consider the main parts of the human body involved in these procedures, such as the meninges and the cerebrospinal fluid, which protect the central nervous system. As it is well known, the meninges are comprised by three layers: the dura mater, the arachnoid and the pia mater. The dura mater is the outermost, strongest, non-flexible layer from those three; the arachnoid is the medium membrane and the pia mater is the innermost and fragile of the meninges layers. In turn, the cerebrospinal fluid is a clear bodily fluid occupying the subarachnoid space, which is the space between the arachnoid and pia mater layers in the meninges.

The insertion of a hollow spinal needle (e.g., a Tuohy needle) is used in the Epidural anesthesia until the epidural space has been reached, being the space located underneath the dura mater. Firstly, the area wherein the needle is inserted is blocked with local anesthesia. Then, the needle is inserted and removed after the catheter has passed through the epidural space, said catheter remains in this area. The anesthetic is injected in the catheter to block the body area either upwards or downwards the injection point, as needed. In case it is necessary to apply more anesthetic, the catheter is secured over the patient's back to be reused again.

However, as the dura mater and arachnoid layers are so close to each other, sometimes it is not possible to pierce the dura mater without piercing the arachnoid with the epidural anesthetic, then, in this kind of procedures, it is of the outmost importance for the surgeon to be very precise.

In the same way as above, the subdural or subarachnoid anesthesia is carried out except that the anesthetic is directly injected in the cerebrospinal fluid surrounding the spinal cord with the aid of a second spinal needle, such as a Whitacre needle, a Quinkle or a Sprotte needle, this needle being introduced into the first spinal needle (Tuohy needle). The subdural or subarachnoid anesthesia blocks the body part beneath the site wherein the anesthetic is delivered, or, above it, depending on the anesthetic dose and the technique used for its application. In other words, if the tip of the second needle is directed towards the body's upper part and the anesthetic is delivered therein then this body's part will be blocked and the same will occur when the anesthetic is delivered to the body's lower part. Sometimes, to carry out a continuous spinal anesthesia, instead of using the second needle a spinal catheter can be inserted and left in the site where the injection was made.

In fact any spinal needle will pierce the skin, the subcutaneous fat, the supraspinous ligament, ligaments, the epidural space (in the case of the epidural anesthesia), the dura mater and the arachnoid layers until the needle reaches the subarachnoid space wherein the spinal cord and the nerve roots are located, surrounded by the cerebrospinal fluid (in the case of the spinal anesthesia).

On the other hand, there is also the mix anesthesia consisting in the application of both the epidural and the subdural or subarachnoid anesthesia. The first is used in surgery to provide an anesthetic, particularly to deliver reinforcing doses, while the second is used to provide a longer term anesthesia to a patient.

It is very important to ensure that the injection will correctly pierce the desired area with the epidural and subdural or subarachnoid anesthesia, since otherwise the nervous, cardiovascular and respiratory systems may be affected with the anesthetic. Both the epidural and subdural or subarachnoid anesthesia may significantly affect the breathing, the heart beating and other vital functions. Moreover, there is a potential toxicity risk caused by high drug doses unnecessary to obtain a proper blocking. As mentioned above, in order to achieve the object of blocking the desired part of the body, the anesthetic flow direction dosed in the epidural or subarachonid space is very important.

In specific relation to the epidural anesthesia, techniques and devices have been developed in the prior art to locate the epidural space, being that known as "loss-of-resistance" the most common technique used in the prior art wherein a spinal needle such as a Tuhoy needle, is connected to a syringe wherein its plunger is initially offset to leave inside the syringe housing from 4 to 10 cubic centimeters of air. Then while the plunger stem end is pressed with the thumb to exert a slight pressure, the needle is introduced into the patient's body. In this manner, the reaching of the epidural space is indicated by a lower pressure than that existing within the needle, causing the syringe plunger to travel without resistance in the patient's direction.

However, the above technique has to be carried out very carefully, since as the dura mater and arachnoid layers are so close to each other as already mentioned, sometimes it is not possible to pierce the dura mater without piercing the arachnoid layer. Further, there is a risk of introducing an excess of air into the epidural space which may cause injuries to the patient.

A system to increase the visibility in the epidural space is disclosed in the U.S. Pat. No. 6,925,323. Said document discloses an epidural surgery method to enhance the visibility in a patient's epidural space, having the object of effectively carrying out the therapeutic surgery in said space. The method includes the steps of distending a patient's epidural space portion by filling said epidural space portion with a fluid supplied from a catheter; placing a sight hole in the epidural space distended portion by inserting the sight hole through the same catheter supplying the fluid making the distention, thereby achieving a visual image of the epidural space.

The U.S. Pat. No. 5,902,273 discloses a syringe capable of being pressured for the identification of the epidural space, this syringe is characterized by comprising a piston descending within a housing located in the needle upper part, visually indicating the surgeon the time when the needle has reached the epidural space. In the invention of this document, it is required that the surgeon places his/her finger in the distal end of the syringe to detect the pressure drop, which is visually checked with the movement of said piston.

The U.S. Pat. No. 6,773,417 shows an epidural space locating device comprising a body section having a first end and a second end; a channel extending between said ends wherein the first end may be coupled to a luer connector; and a collapsible rear chamber having one end coupled to the second end of the body section and the other end is exposed such that it allows exerting a pressure with one or more fingers of the hand such that the chamber keeps its shape when there is a positive pressure in it, and on the other hand, the chamber collapses when there is a negative or cero pressure in it indicating the location of the epidural space through a needle coupled to a luer connector; and the pressure loss within the chamber is detected by the fingers of the hand as the shape of the chamber collapses. Again, in the distal end of this device, a pressure has to be exerted.

Furthermore, it is worth mentioning the U.S. Pat. No. 7,175,608, wherein a device is provided to be placed between a syringe and the spinal needle; this device allows the visual detection of the time when the spinal needle has reached the epidural space by including a diaphragm which swollen when pressurized, and becoming depressurized when the needle has reached the epidural space.

As may be seen, the prior art devices still uses or are related to a syringe or a media wherein pressure has to be applied with the fingers, moreover, when the syringe and the spinal needle are coupled to each other, several centimeters in length can result, being a disadvantage in the management of the needle and the device once coupled since the weight may break the coupling, therefore, there is still a need for more precise, compact instruments and devices which allows the surgeon to detect the time when the epidural space has been reached.

BRIEF DESCRIPTION OF THE INVENTION

A device has been designed for the location of the epidural space in order to overcome the prior art drawbacks and above all, to effect the correct location thereof. The device comprises a handle with a distal end and a proximal end; a hollow distal chamber attached to the handle distal end and being provided with a connector wherein a spinal needle is received which is to be introduced in the patient's body, such that there is a fluid connection between the spinal needle and the distal chamber. A detection system of pressure loss or drop is a further element of the device of the present invention which comprises a plunger running within the distal chamber from a starting position to a final position when there is a pressure loss caused when the spinal needle has reached the epidural space; and means to signaling the pressure drop within the distal chamber, and connected to the plunger; such that said means generates a warning signal when the plunger moves to its final position because the needle has reached the epidural space.

In the present invention, means are provided to secure the plunger in its starting position. Such as its name suggests, the purpose of the securing means is to immobilize the plunger at the time the spinal needle couples with the device, once the device and the spinal needle are coupled, and when the spinal needle is into the patient, the securing means are released so the plunger can freely move within the distal chamber for the time when the spinal needle reaches the epidural space.

In turn, the warning signal which may be visual, tactile, or audio type, or a combination thereof, is generated from a signal generating source, preferably, a visual signal in the form of light is generated, preferably emitted by a signal generating source such as a light emitting diode (LED).

The device of the present invention may be disposable or reusable, and a transparent distal chamber is preferred. With the device of the present invention, the epidural space is located in a more reliable manner with respect to the prior art techniques and devices.

BRIEF DESCRIPTION OF THE DRAWINGS

The novel aspects considered characteristics of the present invention will be particularly set forth in the appended claims. However, the invention itself, both for its organization and for the structural arrangement of the elements and pieces thereof, together with other objects and advantages, will be better understood from the following detailed description of a preferred embodiment of the invention, when read in relation to the drawings wherein:

DETAILED DESCRIPTION OF THE PREFERRED EMBODIMENT OF THE INVENTION

Figure 1:
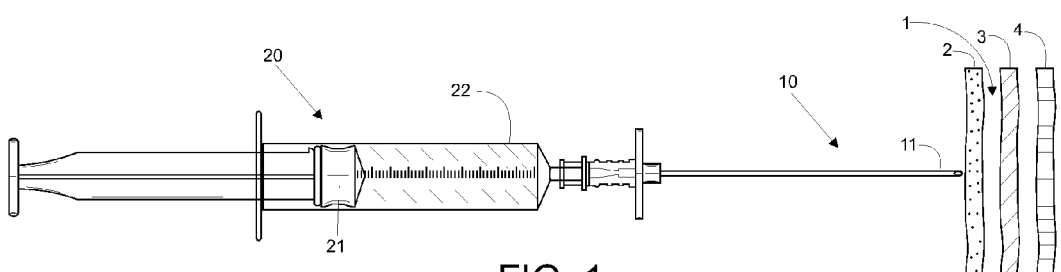
FIG. 1 is a side view of a syringe and a spinal needle, the syringe being specially designed to carry out the "loss-of-resistance" technique used in the prior art to detect the epidural space.
Figure 3:
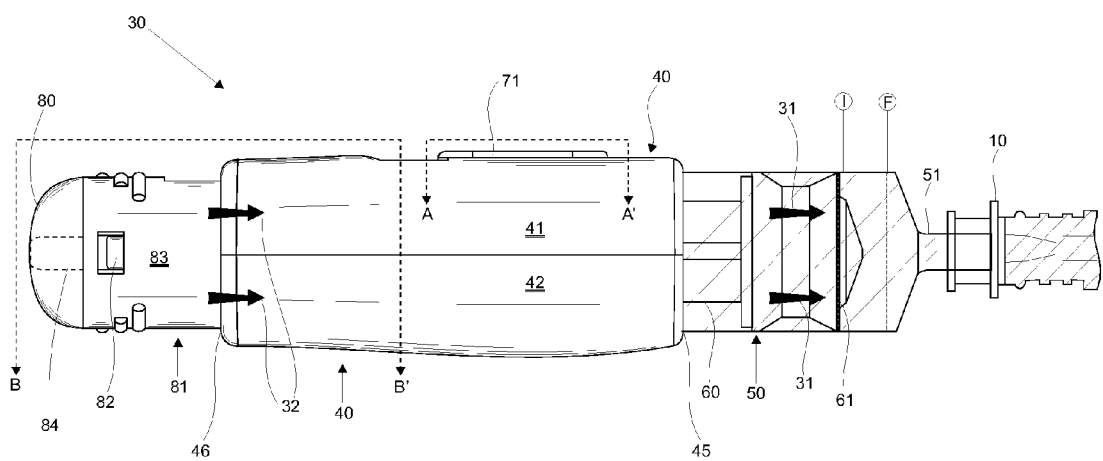
FIG. 3 is a side view of a preferred embodiment of the epidural space locating device of the present invention.

In order to clearly appreciate the advantages and differences of the present invention with respect to the prior art, reference is made to FIGS. 1 and 3 to describe the technique named "loss-of-resistance" wherein a spinal needle 10 of the Tuhoy type and a syringe 20 coupled to the spinal needle 10 are used. In FIG. 1, the plunger 21 of the syringe 10 is offset towards the housing proximal end 22 of the syringe 20 since there is a volume of air therein, i.e., the cannula 11 of the syringe 10 has not reached the epidural space 1 located between the dura mater 2 and the arachnoid 3 membranes. The numeric reference 4 corresponds to the pia mater membrane.

Figure 2:
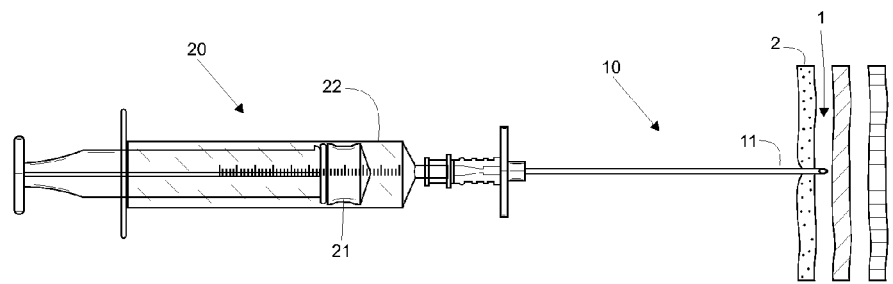
FIG. 2 is a side view of the syringe and the spinal needle of FIG. 1, once the needle has reached the epidural space.

FIG. 2 illustrates the time when the cannula 11 of the syringe 10 has pierced the dura mater 2 and has reached the epidural space 1 wherein there is a lower pressure with respect to that existing within the syringe 20, an accordingly the plunger 21 of the syringe 20 travels without any resistance within the housing 22 and towards the patient, i.e, it travels in the distal direction since the proximal direction is that nearest the user managing the syringe 20, such as an anesthesiologist.

Now, reference is made to FIG. 3 in the appended drawings wherein an epidural space locating device referred as 30, is seen. The device is construed according to a preferred embodiment of the present invention, which embodiment should be considered as illustrative only and not limitative of the present invention. The device 30 comprises a handle 40 having a distal end 45 and a proximal end 46, the handle is preferably hollow and cylindrically shaped formed by an upper half 41 and a lower part 42 coupled to each other. At right side in FIG. 3, a hollow distal chamber 50, also cylindrically shaped, may be seen. The distal chamber 50 is attached to the distal end 45 of the handle 40 and is provided with a distal connector 51 wherein a spinal needle 10 is received, which is introduced into the patient's body, such that there is a fluid connection between the spinal needle 10 and the distal chamber 50. The distal connector 51 is preferably a "luer" type connector, which is well known in the art and a further description thereof is herein considered unnecessary.

Another element of the device of the present invention may also be seen In FIG. 3, being a plunger 60 with a rubber head 61 running within the distal chamber 50, from a starting position marked with the letter "I" to a final position marked as "F". When there is a pressure loss in the distal chamber 50 caused by the spinal needle 10 having reached the epidural space, the plunger 60 moves in the distal direction, such as indicated by the movement arrows 31. Herein, it is important to remark that at the time of the beginning of a pressure loss within the distal chamber 50, the plunger 60 moves in the distal direction, thus implying that the epidural space has been reached. The starting "I" and final "F" positions in FIG. 3 are illustrative only and represent the movement of the plunger 60, said movement may have a longer or shorter stroke.

As mentioned above, the device of the present invention comprises means to secure the plunger 60 in its starting position "I", in particular, a pivoting button 71 mounted on the handle 40 is shown in FIG. 3, said button 71 is part of said securing means. Further elements of the securing means for the preferred embodiment will be described below.

In the present invention, is most importance to warning the user the time of reaching the epidural space, and therefore, signaling means are provided which are connected to the plunger 60. In this regard, at the left side of the proximal end 46 of the handle 40, some elements forming the signaling means are seen, such as the moving compartment 81, formed by an inner body 82 and a lid 83 coupled to each other. Inside the moving compartment 81, there is a light emitting diode (LED) 84 (illustrated in dashed lines); said compartment 81 is attached to the plunger 60, such that if the plunger 60 moves in the distal direction since the spinal needle 10 has reached the epidural space, the compartment 81 also moves, which, as being introduced in the handle 40 as illustrated by the movement arrows 32, turns on the LED 84, which light may be seen through the proximal end 80 of the moving compartment 81. It is to be noted that there are other internal elements of the signaling means which will be described below. The signaling means and the plunger are the two parts forming the pressure loss or drop detection system in the locator of the present invention.

Figure 4:
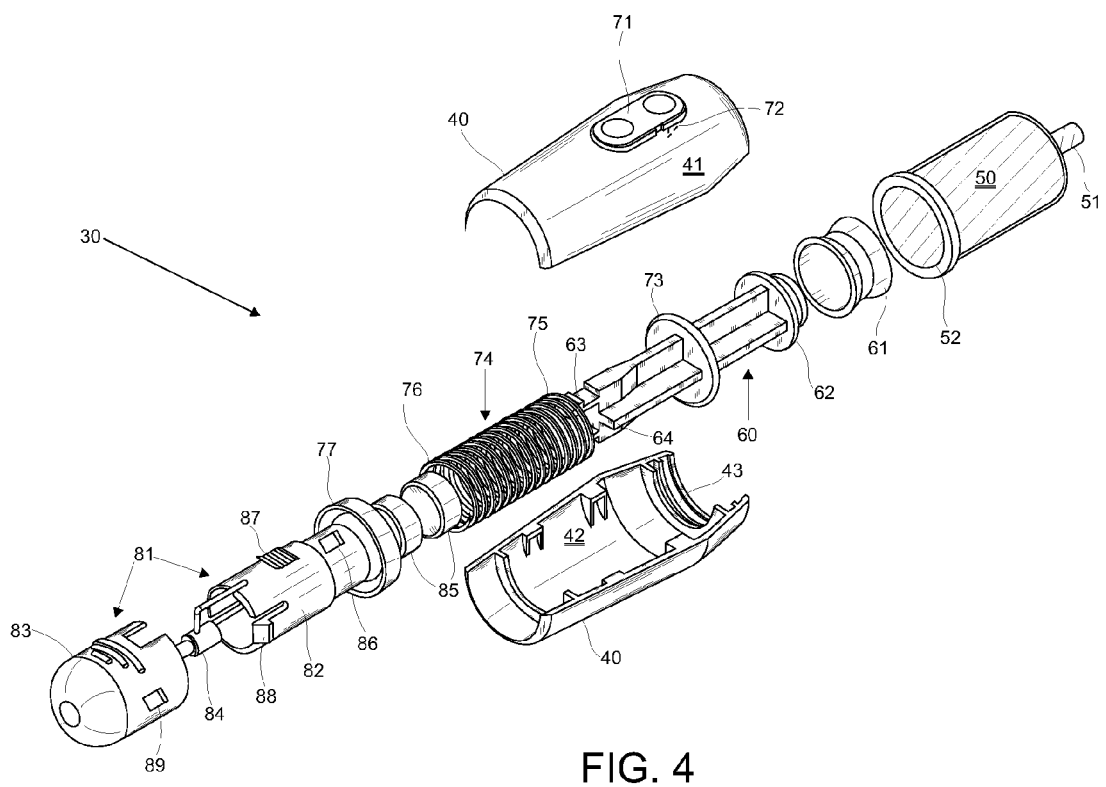
FIG. 4 is an exploded view of the epidural space locating device illustrated of FIG. 3.

Now, reference is made to FIG. 4 showing an exploded view of the epidural space locating device 30, which parts are clearly distinguished in this Figure, e.g., the upper half 41 and the lower half 42 of the handle 40 coupling to each other may be seen. Likewise, the distal chamber 50 is shown, being preferably transparent and having a proximal end 52 in a ring shape which is received inside a distal inner seat 43 of the handle 40. Within the distal chamber 50 travels the plunger 60 having an elongated shape. A rubber head 61 is mounted on the distal end 62 of the plunger 60, dimensionally fitting to the distal chamber 50 interior to seal it.

As may be seen, in the upper half 41 of the handle 40, a pivoting button 71 is included having a "securing" position and a "releasing" position. The button 71 is provided with a lowering projection 72, which engages on an annular disc 73 provided on the plunger 60 to secure it; the annular disc 73 is pressed against the projection 72 by elastic means, which in the embodiment being described is the spring 74 mounted inside the handle and which distal end 75 contacts the disc 73. In addition, the spring 74 has a proximal end 76 contacting the stopper 77 to lean on. In this manner, before the device is used, the plunger is secured by the button 71 engaging on the disc 73, and to keep it in its starting position receives a slight force from the spring 74; then, while moving the button 71 to the free position, the projection 72 is withdrawn from the disc 73 of the plunger 60 such that when a pressure loss exists therein, this latter can freely move within the distal chamber 50. The button 71, the lowering projection 72, the annular disc 73 and the spring 74 form the securing means in the embodiment being described.

As mentioned above, a detection system for the pressure loss or drop is provided in the present invention, one part of said system is the signaling means connected to the plunger, which indicates the user the pressure drop within the distal chamber, such that said means generates a warning signal when the needle has reached the epidural space. In this embodiment, the signaling means comprises the moving compartment 81 formed by the inner body 82 and the lid 83, coupling to each other; inside the compartment 81 an energy source is housed, such as batteries 85; the compartment 81 is connected to the plunger 60 by means of coupling legs 63 included in the proximal end 64 of the plunger 60, the coupling legs 63 freely run inside the spring 74 and the stopper 77, to be inserted in the coupling openings 86 included in the inner body 82 of the moving compartment. When the plunger 60 and the moving compartment 81 are attached to each other, this latter can move inside and outside the proximal end 46 of the handle 40.

A further part of the signaling means is the switch 87 electrically connected to the batteries 85 and to the LED 84, the switch has a form of a leaf spring and it is mounted on the moving compartment 81. The switch 87 closes once the plunger 60 has reached its final position in order to turn on the LED 84 being fed by the batteries 85. The inner body 82 and the lid 83 are attached to each other by coupling projections 88 provided in the inner body 82, said coupling projections 82 are inserted in the windows 89 formed in the lid 83.

Figure 5:
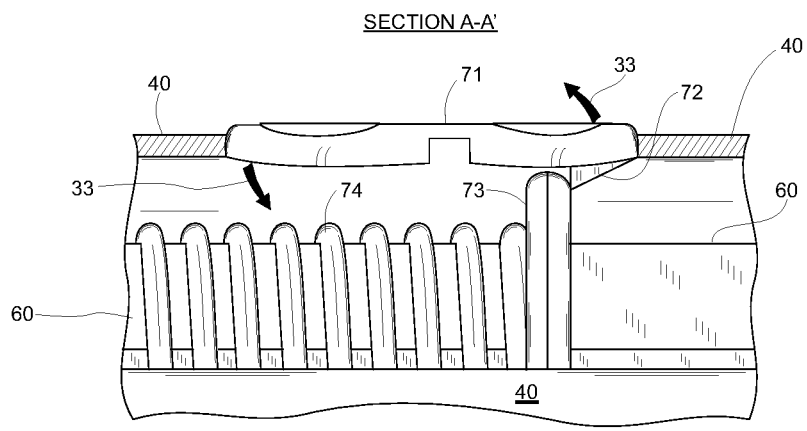
FIG. 5 is an enlarged cross-section view taken along line A-A' of the epidural space locating device of FIG. 3.

Now, to describe further the securing means, emphasis is made to FIG. 5. The securing means comprises a pivoting button 71 mounted on the handle 40, with its lowering projection 72 having a tooth shape. The projection 72 contacts one face of the annular disc 73, which is slightly pressed by the spring 74, in which interior freely runs the plunger 60. By pressing the button 71 in this manner as shown by the lowering movement arrow 33, the annular disc 73 is released so the plunger 60 can freely move in the distal direction. When the button 71 is released, the plunger 60 does not move as there is an air pressure within the distal chamber; only when there is a pressure loss in the distal chamber, occurs the plunger movement.

Figure 6:
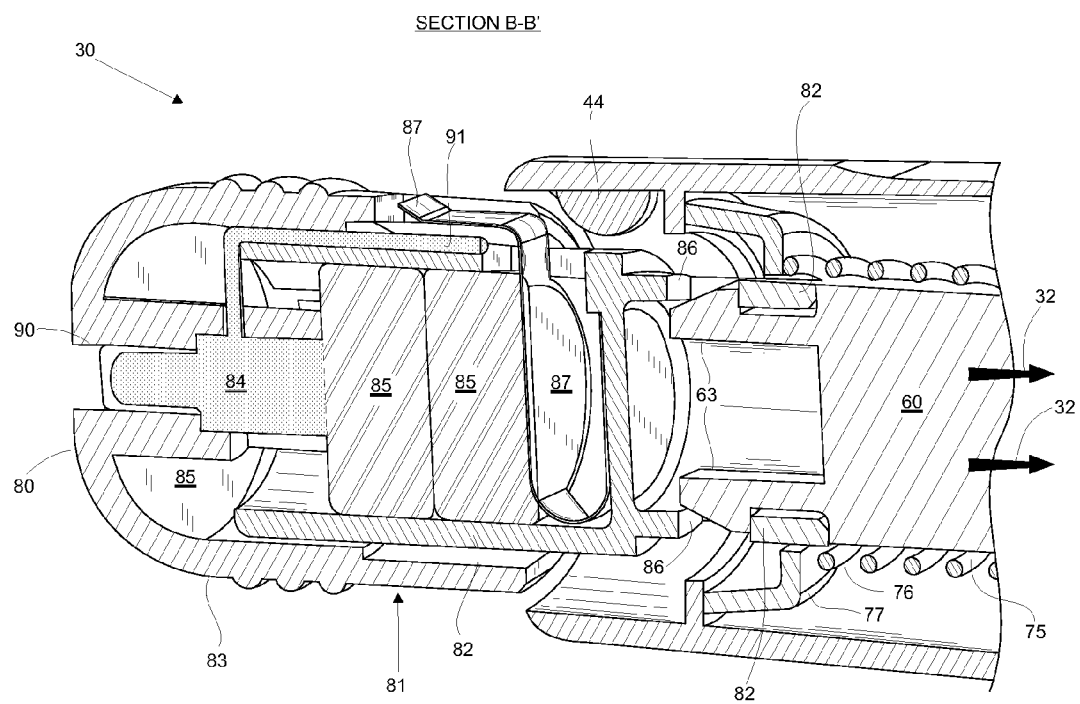
FIG. 6 is an enlarged cross-section view taken along line B-B' in FIG. 3, wherein the plunger is located in the starting position.
Figure 7:
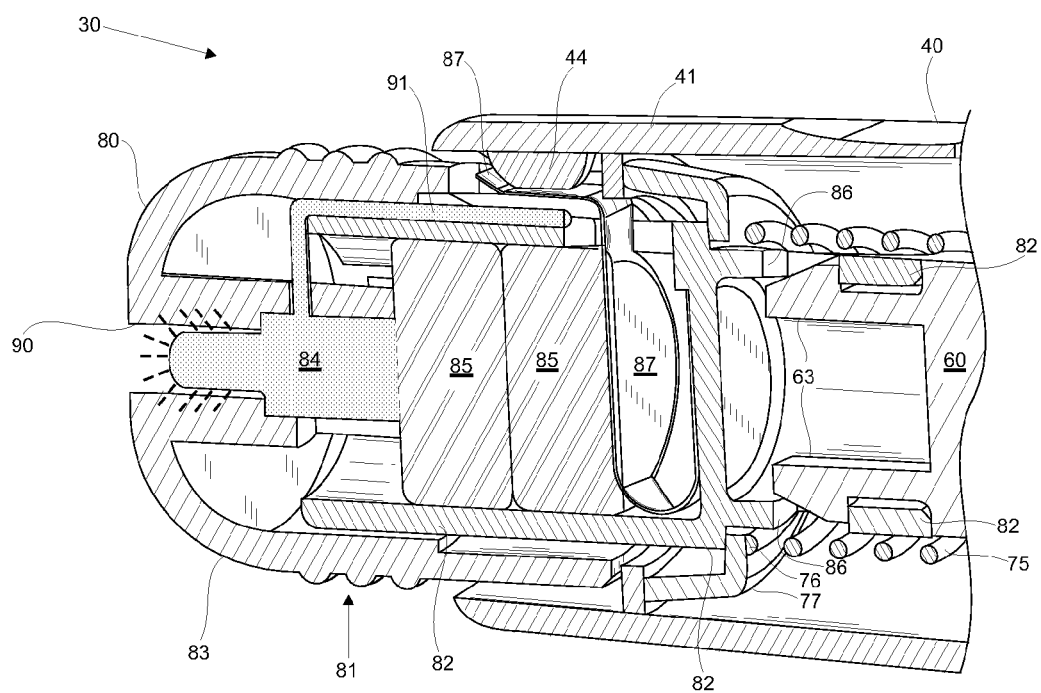
FIG. 7 is an enlarged cross-section view taken along line B-B' in FIG. 3, wherein the plunger is located in the final position.

In order to describe in detail how to detect and warn that the spinal needle has reached the epidural space, reference is made to FIGS. 6 and 7 showing cut views of the proximal end of the epidural space locating device 30. FIG. 6 corresponds to the starting position of the plunger 60, while FIG. 7 corresponds to the final position of the plunger 60 when the epidural space has been reached. As mentioned above, the plunger 60 is attached to the moving compartment 81 by means of coupling legs 63 being inserted in the coupling openings 86 included in the inner body 82 of the moving compartment 81, thereby, when the plunger 60 moves such as shown by the arrows 32, the moving compartment also moves in the distal direction, closing the switch 87 to turn on the LED 84 which is fed by the batteries 85. Particularly, the handle 40 includes a semi circularly-shaped inner edge 44 provided in the upper half 41, which causes the lowering of the switch 87, as the moving compartment 81 is introduced to contact the switch 87 with the terminal 91 of the LED, to turn on this latter, which light may be seen through a proximal window 90 provided in the proximal end 80 of the lid 83, said lid 83 may also be transparent to see the LED light 84. The spring 74 is also shown in FIGS. 6 and 7 which proximal end 76 leans on the stopper 77.

As may be seen from the described embodiment, the warning signal is a visual signal, and the signal emitter source is a LED, however, if the generation of a tactile signal is desired, the LED may be substituted by a vibrating motor, or if the generation of an audio signal is preferred, a speaker emitting sounds is mounted instead of a LED; there are multiple possibilities.

Due to its medical use, the locating device of the present invention is sterilized with gamma rays or ethylene oxide, and it is manufactured from plastic materials in order to make it cheap and disposable.

Although in the above description reference is made to a single embodiment of the invention, several modifications are possible to such embodiments without departing from the true scope of the invention. Therefore, the present invention may not be restricted but for that stated in the prior art and by the spirit of the appended claims.

The invention claimed is:

1. An epidural space locating device, comprising:
   a) a handle with a proximal end and a distal end;
   b) a hollow distal chamber attached to the distal end of the handle, the hollow distal chamber being provided with a distal connector wherein a spinal needle is received such that there is a fluid connection between the spinal needle and the distal chamber, the spinal needle being configured to be introduced to a patient's body;
   c) a pressure loss or drop detection system comprising a plunger running within the distal chamber from a starting position to a final position, and a signaling device connected to the plunger;
   d) a pivoting button mounted on the handle for securing the plunger in said starting position;
   e) an annular disc around the plunger for securing the pivoting button on a securing position when a lowering projection, provided on the button, engages the annular disc; and
   f) elastic means pressing the disc against the lowering projection
   wherein, when the spinal needle is introduced into the patient's body, the lowering projection withdraws from the annular disc and moves the pivoting button to a released position to release the plunger, and once the spinal needle has reached the epidural space, a pressure loss is produced into the distal chamber, thereby moving the plunger in a distal direction towards said final position, and activating the signaling device to generate a warning signal that the needle has reached the epidural space.

2. An epidural space locating device according to claim 1, wherein the elastic means is a spring.

3. An epidural space locating device according to claim 1, wherein the warning signal generated when the plunger moves towards its final position is a visual, tactile, or audio signal, or a combination thereof.

4. An epidural space locating device according to claim 1, wherein the distal connector of the distal chamber is a luer type connector.

5. An epidural space locating device according to claim 1, wherein the distal chamber is transparent.

6. An epidural space locating device according to claim 1, wherein the signaling device comprises:
   i) a moving compartment wherein an energy source is housed, the compartment being attached to the plunger, the compartment travels inside and outside the proximal end of the handle;
   ii) a switch mounted on the compartment and closing once a piston of the plunger has reached a final position; and
   iii) a signal generating source mounted on the compartment and electrically connected to the energy source and switch, the signal generating source is activated when the switch closes to generate the warning signal indicating the epidural space has been reached.

7. An epidural space locating device according to claim 6, wherein the energy source is a battery.

8. An epidural space locating device according to claim 6, wherein the moving compartment is formed by an inner body attached to the plunger and a lid coupled to the inner body, wherein through the lid the warning signal is perceivable.

9. An epidural space locating device according to claim 8, wherein the lid is transparent.

10. An epidural space locating device according to claim 6, wherein the warning signal is a visual, tactile, audio signal or a combination thereof.

11. An epidural space locating device according to claim 10, wherein the warning signal is a visual signal.

12. An epidural space locating device according to claim 11, wherein the generated visual signal is a light.

13. An epidural space locating device according to claim 10, wherein the generated warning signal is a tactile signal.

14. An epidural space locating device according to claim 13, wherein the tactile signal is generated by a vibrating motor.

15. An epidural space locating device according to claim 10, wherein the generated signal is an audio signal.

16. An epidural space locating device according to claim 15, wherein the audio signal is a speaker emitting sounds.

* * * * *